United States Patent [19]

Warner, Jr. et al.

[11] 4,172,947
[45] Oct. 30, 1979

[54] 1-(2-ACYLAMINOPHENYL)IMIDAZOLES

[75] Inventors: Paul L. Warner, Jr., Clarence; Edward J. Luber, Jr., Buffalo, both of N.Y.

[73] Assignee: Westwood Pharmaceuticals, Inc., Buffalo, N.Y.

[21] Appl. No.: 858,514

[22] Filed: Dec. 8, 1977

Related U.S. Application Data

[63] Continuation-in-part of Ser. No. 757,640, Jan. 7, 1977, abandoned.

[51] Int. Cl.² .................................. C07D 233/60
[52] U.S. Cl. .................... 548/346; 542/421; 544/346; 424/250
[58] Field of Search ................. 548/346; 542/421

[56] References Cited

U.S. PATENT DOCUMENTS

| | | | |
|---|---|---|---|
| 3,541,109 | 11/1970 | Kauer | 548/346 |
| 4,011,236 | 3/1977 | Grier | 542/421 |

OTHER PUBLICATIONS

Simonov et al., Chem. of Heterocyclic Cpds., May 15, 1974, pp. 380–382.

Wilkinson et al., Chem. Abst., 1975, vol. 82, No. 39231u & 9th Coll. Index, p. 16512cs.

Cardellini et al., Farmaco, Ed. Sc., 1975, vol. 30(7), pp. 536–545.

*Primary Examiner*—Alan L. Rotman
*Assistant Examiner*—Natalia Harkaway
*Attorney, Agent, or Firm*—Morton S. Simon; Irving Holtzman

[57] ABSTRACT

A 1-(2-acylaminophenyl)imidazole of formula:

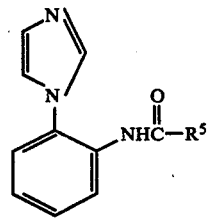

wherein $R^5$ is hydrogen or an aliphatic, cycloaliphatic, phenyl, substituted phenyl, fused bicyclic aryl or monocyclic aryl substituted aliphatic group bonded to the carbonyl carbon through a carbon-to-carbon linkage. The compounds are useful as intermediates in the preparation of 4-substituted imidazo[1,2-a]quinoxalines.

24 Claims, No Drawings

1-(2-ACYLAMINOPHENYL)IMIDAZOLES

RELATED CASES

This is a continuation-in-part of application Ser. No. 757,640 filed Jan. 7, 1977, now abandoned.

This invention relates to certain 4-substituted imidazo[1,2-a]quinoxalines and to processes for preparing the same. It also concerns certain 1-(2-acylaminophenyl)imidazoles which among other things are useful as intermediates in the preparation of 4-substituted imidazo[1,2-a]quinoxalines. The aforesaid compounds are useful for a variety of purposes which will be described in more detail below. Some of these are useful as immunosuppressants; whereas, others are useful as anti-inflammatory agents or display antifungal activity. Moreover, some exhibit two or all three of these activities.

The 4-substituted imidazo[1,2-a]quinoxalines encompassed in the present invention may be described by the formula:

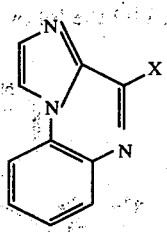

I and pharmaceutically acceptable salts thereof wherein X is —$R^1$ or —$NHR^2$ wherein:

(1) $R^1$ is bonded to a ring carbon by a carbon-to-carbon linkage and is an aliphatic, cycloaliphatic, substituted phenyl, fused bicyclic aryl, or monocyclic aryl-substituted aliphatic; and (2) $R^2$ is a radical bonded to a nitrogen by a carbon to nitrogen linkage; said radical being selected from the group consisting of aliphtic, cycloaliphatic, phenyl, substituted phenyl, fused bicyclic aryl or a monocyclic aryl-substituted aliphatic group.

When $R^1$ is an aliphatic group, it may be a straight chain or branched chain hydrocarbon group which is saturated, monounsaturated or polyunsaturated. It may also comprise a straight chain or branched chain group containing other than carbon-to-carbon bondings e.g. ether linkages, carbon to halogen linkages, etc. Ordinarily, it will contain from about 1 to 18 carbon atoms, the most typical radicals of this group being the alkyl radicals having from 1 to 18 carbon atoms.

By way of illustrating the aliphatic groups that may be represented by $R^1$, the following are given: $CH_3$—; $CH_3CH_2$—; $CH_3CH_2$—$CH_2$—; $CH_3(CH_2)_n$— in which n is 3, 4, 5, 6, 7, 8, 14 and 16 respectively; $(CH_3)_2CH$-$CH_2$—; $CH_3(CH_2)_3(CH_3CH_2)CH$—, $CH_2$=$CH$—$(CH_2)_8$—, alkoxyalkyl in which the alkyl moieties have from 1 to 4 carbon atoms e.g. methoxymethyl; halogenoalkyl (i.e. $CH_2Cl$—; $CH_3CHCl$—; $CHCl_2$—; $CCl_3$—; $CH_2Br$—; $CF_3$).

When $R^1$ is a cycloaliphatic radical it will most often be a cycloalkyl radical containing 3 to 8 carbon atoms or a cycloalkenyl radical containing 5 to 6 carbon atoms. By way of illustrating the cycloaliphatic radicals that may correspond to $R^1$ in formula I mention may be made of the cyclopropyl

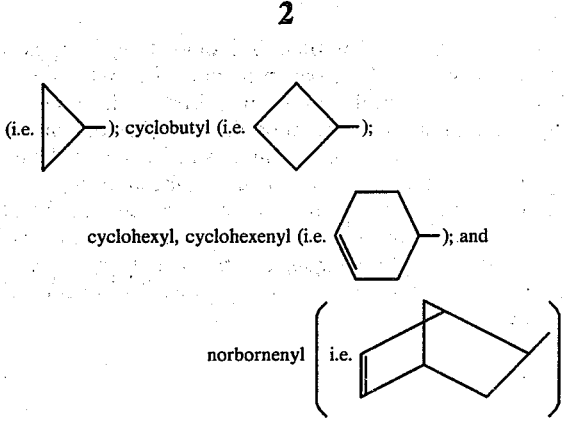

When $R^1$ is a substituted phenyl radical in formula I above, the phenyl group may have from 1 to 5 substituents but will usually be mono, di or trisubstituted. Typical among the groups that may be contained in the phenyl group are (a) alkyl groups which are branched or straight chain containing 1 to 6 carbon atoms e.g. methyl, ethyl, tertiary butyl; (b) alkoxyl groups containing 1 to 6 carbon atoms e.g. methoxy, ethoxy; (c) hydroxy; (d) acyloxy containing 1 to 18 carbon atoms; (e) halogen e.g. 1 or 2 Cl, F, Br, I preferably in the meta and/or para position; (f) nitro; (g) amino; (h) acylamino in which the acylamino moiety is derived from an alkanoic acid containing 1 to 18 carbon atoms and benzamides in which the benzene ring is unsubstituted or monosubstituted, disubstituted or trisubstituted with alkyl groups containing 1 to 5 carbon atoms or halogen atoms; (i) polyhydroxyalkylamino groups containing 4 to 8 carbon atoms; (j) cyano; (k) trifluoromethyl; (l) mercapto; (m) alkylthio; (n) acylthio containing 1 to 18 carbon atoms; (o) carboxyl; (p) carboalkoxyl containing 1 to 8 aliphatic carbon atoms; (q) phenyl; (r) phenoxy, and combinations thereof.

When $R^1$ is a fused bicyclic aryl radical, it may be a substituted or unsubstituted radical. These are exemplified by such fused bicyclic hydrocarbon radicals as 1-napthyl, 2-napthyl etc.

When $R^1$ is a monocyclic aryl substituted aliphatic radical, the monocyclic aryl moiety may be either of the substituted or unsubstituted variety. The aliphatic moiety of this group may be either of the saturated or unsaturated straight chain or branched chain hydrocarbon variety or it may contain other than carbon-to-carbon bonding. This may be illustrated by such groups as phenoxymethyl; benzyl, styryl,

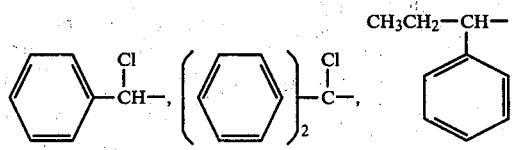

The group $R^2$ in the radical —$NHR^2$ of formula I above is exemplified by the same radicals given above in illustrating the radical —$R^1$. In addition, $R^2$ may also be phenyl as in the case of the

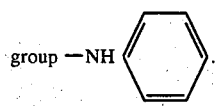

In general, the compounds included in formula I above as well as the cases in formula I in which X is hydrogen or phenyl may be prepared by heating the corresponding 1-(2-acylaminophenyl)imidazole at reflux in the presence of cyclizing quantities of a cyclizing agent e.g. polyphosphoric acid or phosphorous oxychloride, etc. for sufficient time to cause significant cyclization of this reactant. More particularly, the 1-(2-acylaminophenyl)imidazole reactants that can be employed in this process may be described by the general formula:

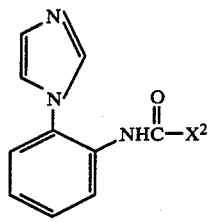

II in which $X^2$ is $R^5$ or $-NHR^2$ wherein:

$R^5$ is hydrogen or an aliphtic (preferably $C_1$ to $C_{17}$), cycloaliphatic, phenyl or substituted phenyl, fused bicyclic aryl or monocyclic aryl substituted aliphatic radical and $R^2$ has the same values assigned to it in connection with formula I above.

The group $R^5$ in formula II is illustrated by the same groups that illustrate $R^1$ in formula I. However, in addition, $R^5$ may also be illustrated by the phenyl radical.

The reaction can be depicted by the following equation:

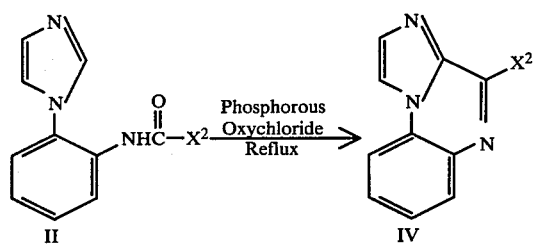

III

The process of equation III is preferably carried out in the presence of an excess of an organic amine solvent. A variety of solvents may be used for this purpose among which mention may be made of the following: pyridine, 2,6-dimethylpyridine, N,N-dimethylaniline, trimethylamine, and N-methylmorpholine, etc. However, the preferred organic solvent is pyridine.

The quantity of phosphorous oxychloride that is employed in the reaction can vary somewhat. Generally, however, the phosphorous oxychloride will be employed in the range of from about one-half mole to about 6 moles and preferably one-half mole to two moles per mole of compound II.

The desired product IV may be recovered from the reaction mixture using any of the ordinary techniques well known to those skilled in this art. The time of reaction will vary depending upon, among other things, the particular reactants or molar quantities of reactants employed. In general, the reaction time will be from about 30 to 120 minutes.

The temperature employed in carrying out the reaction will also vary depending upon the particular reactants selected, the solvent and other factors. Ordinarily, the temperature employed will be the reflux temperature of the reaction mixture. This generally will be in the range of from about 95° C. to 195° C.

The method of preparing the 1-(2-acylaminophenyl)imidazoles (compound II) will vary depending on the particular type that is being made. Thus, for example, in preparing compound of the general type:

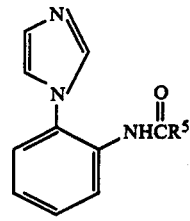

V where $R^5$ is hydrogen, aliphatic, cycloaliphatic, phenyl, substituted phenyl, fused bicyclic aryl or monocyclic aryl substituted aliphatic group, the 1-(2-acylaminophenyl)imidazole is reacted with the appropriate acid halide e.g. the acid chloride.

This can be expressed by the following equation:

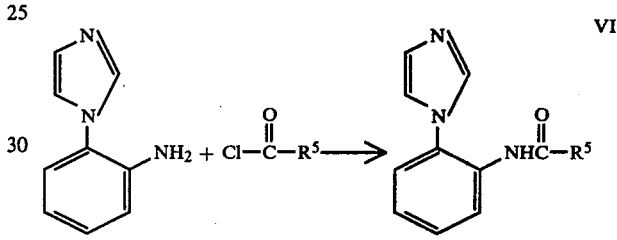

VI in which $R^5$ has the value ascribed to it above. The reaction will usually be carried out employing equimolar amounts of the appropriate acid chloride and in the presence of excess solvent (e.g. pyridine) at reflux.

When the compounds in question are of the phenylureylene type e.g.

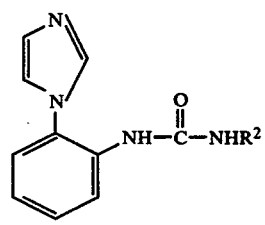

VII wherein $R^2$ is hydrogen, aliphatic, cycloaliphatic, phenyl, substituted phenyl, fused bicyclic aryl or monocyclic aryl substituted aliphatic group, these are prepared by reacting the aminophenylimidazole with the appropriate isocyanate. This can be expressed by the following equation:

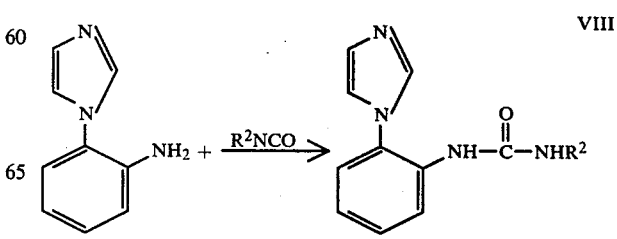

VIII in which $R^2$ has the value ascribed to it above. This reaction is preferably carried out in the presence of a solvent and at steam bath temperatures. A typical solvent that can be employed is toluene and the reactants are usually used in about equimolar quantities. The products obtained from reactions VI and VIII may be recovered using standard techniques well known to those skilled in this art.

PRIOR ART

U.S. Pat. No. 3,887,566 discloses imidazo[1,2-a]quinoxaline and 4-phenylimidazo[1,2-a]quinoxaline. However, this reference does not disclose the 4-substituted imidazo[1,2-a]-quinoxalines of the present invention nor the process for making these compounds. The activity disclosed in this reference for these compounds is as cardiovascular drugs. There is no disclosure of the fact that these compounds may have immunosuppressant activity, antifungal activity of non-steroidal anti-inflammatory action. It is in fact interesting to note that the unsubstituted imidazo[1,2-a]quinoxaline lacks immunosuppressant activity while the 4-phenylimidazo[1,2-a]quinoxaline has only minor activity which is greatly increased by substitution on the para- and meta-positions on the benzene ring.

Uryukina et al, Khim. Geterotsikl. Soedin., 1972, 1558-60 (See C.A. 78, 58345[i] (1973) discloses the unsubstituted and the 7-methyl, methoxy, and bromo substituted imidazo[1,2-a]-quinoxalines. No 4-substituted products are disclosed nor is any utility disclosed for these compounds.

Kovalev et al, Farmakol. Toksikol (Moscow), 36 (2), 232-238, 1973 (See C.A. 78 154693[a]) also discloses the 7-methoxyimidazo[1,2-a]quinoxaline and suggests the use of this material as an hypotensive aget. This reference likewise does not disclose the 4-substituted imidazo[1,2-a]quinoxalines of the present invention of their utility.

Japanese Patents 10677/74 and 10678/74 disclose certain 4-substituted 1,2-dihydroimidazo[1,2-a]quinoxalines and the fact that these materials are useful as anti-inflammatory agents. These references do not show the unhydrogenated compounds of this invention. Moreover, no immunosuppressant activity or antifungal activity is disclosed.

Siminov et al, Khim. Geterotsikl, Soedin, 7, 570 (1971) (See C.A. 76, 25242[n] 1972) discloses a process for synthesizing imidazo[1,2-a]quinoxaline involving the reduction of 1-(o-nitrophenyl)-2-formylimidazole. This is obviously not related to the process of the present invention.

The following Examples are given to further illustrate the present invention. It is to be understood, however, tht they are not limitative of this invention.

The compounds described in the Tables below were prepared as described. Melting points were obtained by the capillary tube method using a Mel-Temp melting point apparatus and are uncorrected. Ultraviolet spectra were obtained in ethanol solution using a Beckman U.V. Acta III or a Beckman DBG. 1-(2-aminophenyl)imidazole was prepared as reported by A. F. Pozharskii, A. M. Siminov and L. M. Sitkina, Khim. Geterotskl. Soedin. 5, 1916 (1969) [Chem. Abstr., 72 11427[a] (1970)].

Table I below further illustrates the preparation of the aliphatic, cycloaliphatic and monocyclic aryl substituted aliphatic-amidophenylimidazoles of the present invention. Table II further exemplifies the preparation of the aryl (including the fused ring aryl) amidophenylimidazoles of this invention.

Except as noted in Tables I and II, the amides were prepared by reacting equimolar amounts of the appropriate acid chloride with 1-(2-aminophenyl)imidazole in the presence of excess pyridine on a steam bath for 45 minutes. The reaction mixture was then stirred into ice water and the crude product isolated according to one of the following methods.

Method A. If a solid was obtained, it was directly crystallized from the solvent indicated in Table I.

Method B. If an oil was obtained, it was dissolved in a minimum amount of chloroform and passed through an alumina column with the amount of alumina being approximately twenty times the weight of the crude solid; elution was with chloroform. The chloroform was evaporated from the crude product which was crystallized as indicated in Table I.

Method C. If a solution was obtained in the ice water mixture, the pyridine/water azeotrope was removed until the crude product separated. It was then treated as in Method B above.

TABLE I

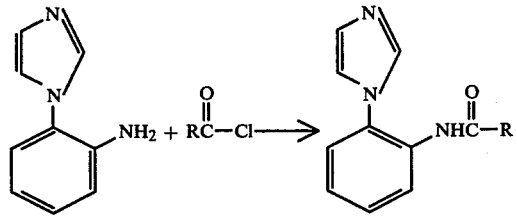

1-(2-alkanamidophenyl)imidazoles

| No. | R | Isolation Method | % Yield | Crystallization Solvent | m.p., °C. | Analysis Calc'd | Found |
|---|---|---|---|---|---|---|---|
| 1 | H—[a] | C | 63.3 | Water | 200–204 | C,64.16 | 64.26 |
|   |   |   |   |   |   | H, 4.85 | 4.71 |
|   |   |   |   |   |   | N,22.45 | 22.30 |
| 2 | CH$_3$— | A | 56.2 | Ethanol | 163–166 | C,65.66 | 65.69 |
|   |   |   |   |   |   | H, 5.51 | 5.52 |
|   |   |   |   |   |   | N,20.88 | 20.84 |
| 3 | CH$_3$CH$_2$—[b] | C | 73.9 | Water | 144–146 | C,66.96 | 67.26 |
|   |   |   |   |   |   | H, 6.09 | 6.15 |
|   |   |   |   |   |   | N,19.52 | 19.40 |
| 4 | CH$_3$(CH$_2$)$_2$— | B | 31.1 | Toluene | 108–110 | C,68.10 | 67.95 |
|   |   |   |   |   |   | H, 6.59 | 6.52 |
|   |   |   |   |   |   | N,18.33 | 18.25 |

TABLE I-continued

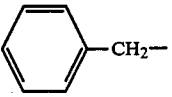

1-(2-alkanamidophenyl)imidazoles

| No. | R | Isolation Method | % Yield | Crystallization Solvent | m.p., °C. | Analysis Calc'd | Found |
|---|---|---|---|---|---|---|---|
| 5 | $CH_3(CH_2)_3$— | B | 49.6 | Toluene-hexane | 123–125 | C,69.11<br>H, 7.04<br>N,17.27 | 69.14<br>7.00<br>17.17 |
| 6 | $CH_3(CH_2)_4$— | B | 49.4 | isopropyl ether-trichloroethylene | 103–105 | C,70.01<br>H, 7.44<br>N,16.33 | 70.31<br>7.45<br>16.26 |
| 7 | $CH_3(CH_2)_5$— | A | 55.3 | isopropyl ether | 96–98 | C,70.82<br>H, 7.80<br>N,15.48 | 70.79<br>7.74<br>15.23 |
| 8 | $CH_3(CH_2)_6$— | A | 55.1 | isopropyl ether | 101–102 | C,71.55<br>H, 8.12<br>N,14.72 | 71.67<br>8.05<br>14.65 |
| 9 | $CH_3(CH_2)_7$— | A | 45.6 | isopropyl ether | 93–95 | C,72.21<br>H, 8.42<br>N,14.03 | 72.24<br>8.41<br>13.92 |
| 10 | $CH_3(CH_2)_8$— | A | 60.6 | isopropyl ether-hexane | 79–81 | C,72.81<br>H, 8.68<br>N,13.14 | 73,38<br>8.85<br>13.02 |
| 11 | $CH_3(CH_2)_{14}$— | B | 58.1 | isopropyl ether | 94–96 | C,75.52<br>H, 9.89<br>N,10.57 | 75.12<br>9.76<br>10.38 |
| 12 | $CH_3(CH_2)_{16}$— | B | 80.6 | isopropyl ether | 98–100 | C,76.19<br>H,10.18<br>N, 9.87 | 76.57<br>10.28<br>9.79 |
| 13 | $(CH_3)_3C$—[b] | C | 48.8 | benzene | 102–104 | C,69.11<br>H, 7.04<br>N,17.27 | 69.15<br>7.26<br>17.19 |
| 14 | $(CH_3)_2CHCH_2$— | C | 25.4 | benzene | 128–130 | C,69.40<br>H, 6.66<br>N,17.34 | 69.60<br>7.00<br>17.40 |
| 15 | $CH_3(CH_2)_3(CH_3CH_2)CH$— | B | 32.8 | benzene | 125–127 | C,71.55<br>H, 8.12<br>N,14.72 | 71.86<br>7.84<br>14.95 |
| 16 | $CH_2=CH-(CH_2)_8$— | A | 76.8 | isopropyl ether-hexane | 92–94 | C,73.81<br>H, 8.36<br>N,12.91 | 74.26<br>8.50<br>12.30 |
| 17 | $CH_3(CH_2)_3(CH_2-CH=CH)_2(CH_2)_7$— | C | 3.6 | [c] | 73.76 | C,76.92<br>H, 9.12<br>N, 9.97 | 76.73<br>9.36<br>9.78 |
| 18 | 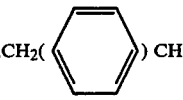—$CH_2$— | C | 41.9 | ethanol | 145.147 | C,73.63<br>H, 5.45<br>N,15.15 | 73.81<br>5.57<br>15.41 |
| 19 | $CH_3CH_2($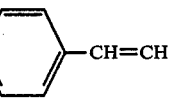$)CH$— | C | 7.7 | diethyl ether | 205–207 | C,74.73<br>H, 6.27<br>N,13.76 | 74.83<br>6.32<br>13.59 |
| 20 | 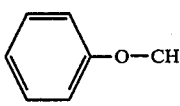—$CH=CH$— | A | 43.0 | ethanol | 161–164 | C,74.72<br>H, 5.23<br>N,14.52 | 74.94<br>5.47<br>14.55 |
| 21 | $CH_3OCH_2$— | A | 49.8 | Toluene | 146–147 | C,62.33<br>H, 5.66<br>N,18.17 | 61.99<br>5.74<br>18.48 |
| 22 | —$O$—$CH_2$ | A | 77.7 | Toluene | 136.5–138.5 | C,69.61<br>H, 5.15<br>N,14.33 | 69.82<br>5.37<br>14.04 |
| 23 | △ | A | 10.1 | isopropanol | 207–209 | C,68.71<br>H, 5.76<br>N,18.49 | 68.67<br>5.85<br>18.67 |

TABLE I-continued

1-(2-alkanamidophenyl)imidazoles

| No. | R | Isolation Method | % Yield | Crystallization Solvent | m.p., °C. | Analysis Calc'd | Found |
|---|---|---|---|---|---|---|---|
| 24 | (cyclobutyl) | A | 55.6 | Toluene | 151–153 | C,69.69<br>H, 6.27<br>N,17.41 | 69.44<br>6.21<br>17.55 |
| 25 | (tetrahydrothiopyranyl) | A | 67.3 | Toluene | 142.5–145 | C,71.35<br>H, 7.11<br>N,15.60 | 70.88<br>6.92<br>15.59 |
| 26 | (cyclohexenyl) | A | 21.6 | ethanol | 196–198.5 | C,72.16<br>H, 6.06<br>N,15.78 | 71.87<br>6.33<br>15.40 |
| 27 | $CH_2Cl-$ | B | 11.9 | water | 255(dec.) | C,56.06<br>H, 4.28<br>N,17.83 | 55.92<br>4.26<br>17.72 |
| 28 | $CH_3CHCl-$ | A | 27.9 | Toluene | 143.5–143.5 | C,57.72<br>H, 4.85<br>N,16.83 | 57.54<br>4.92<br>17.16 |
| 29 | $CHCl_2-$[b] | A | 33.2 | benzene | 162–165 | C,48.91<br>H, 3.36<br>N,15.56<br>Cl,26.25 | 48.94<br>3.24<br>15.42<br>26.17 |
| 30 | $CF_3-$ | A | 22.0 | ethanol | 165–167 | C,51.77<br>H, 3.16<br>N,16.47 | 51.58<br>3.20<br>16.53 |
| 32 | $CH_3CH_2OC(O)-$ | C | 14.1 | trichloroethylene | 128–130 | C,60.23<br>H, 5.05<br>N,16.21 | 60.21<br>5.10<br>16.16 |

Notes:
[a] Prepared from acetic-formic anhydride according to R. J. Jones, J. Am. Chem. Soc., 71,644(1949). After removal by distillation of excess solvent, residue dissolved in water and neutralized with NaOH to provide crude product.
[b] Prepared via the anhydride
[c] Could not be crystallized; purified by chromatography on alumina with ethyl acetate as elutant.

TABLE II

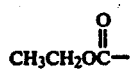

1-(2-Arylamidophenyl)imidazoles

| No. | Ar | Isolation Method | % Yield | Crystallization Solvent | m.p., °C. | λmax.(Am) | Analysis Calc'd | Found |
|---|---|---|---|---|---|---|---|---|
| 34 | (phenyl) | A | 44.9 | dimethoxyethane | 148–150 | 225(21,720) | C,72.99<br>H, 4.98<br>N,15.96 | 73.30<br>5.08<br>16.04 |
| 35 | (m-tolyl, $CH_3$) | A | 58.7 | ethanol | 190–192.5 | 262(21,400) | C,73.63<br>H, 5.45<br>N,15.15 | 73.10<br>5.32<br>15.46 |

TABLE II-continued

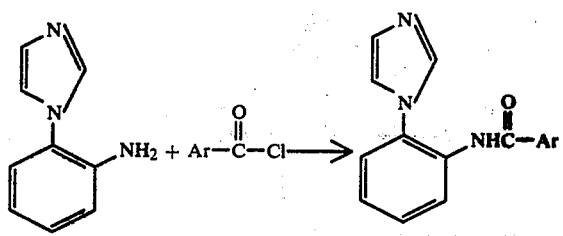

1-(2-Arylamidophenyl)imidazoles

| No. | Ar | Isolation Method | % Yield | Crystallization Solvent | m.p., °C. | λmax.(Am) | Analysis Calc'd | Found |
|---|---|---|---|---|---|---|---|---|
| 36 | (phenyl, 2-CH₃) | B | 58.3 | benzene | 147–148.5 | 231,sh(18,200) | C,73.63<br>H, 5.45<br>N,15.15 | 73.63<br>5.24<br>15.36 |
| 37 | (phenyl, 4-CH₃) | B | 57.4 | benzene | 143–146.5 | 236(23,400) | C,73.63<br>H, 5.45<br>N,15.15 | 73.28<br>5.29<br>15.27 |
| 38 | (phenyl, 3-CF₃) | A | 53.0 | benzene | 151–153 | c | C,61.63<br>H, 3.65<br>N,12.68 | 60.97<br>3.62<br>12.34 |
| 39 | (phenyl, 4-C(CH₃)₃) | B | 79.3 | ethyl acetate | 136–138 | 239(20,400) | C,75.21<br>H, 6.63<br>N,13.27 | 75.06<br>6.45<br>13.31 |
| 40 | (4-biphenyl) | A | 45.5 | isopropanol | 198–200 | 276(28,100) | C,77.86<br>H, 5.05<br>N,12.38 | 77.46<br>4.76<br>12.09 |
| 41 | (phenyl, 4-NO₂) | A | 73.5 | dimethylformamide, ethanol | 194–196 | 260(17,810) | C,62.33<br>H, 3.92<br>N,18.17 | 62.26<br>3.69<br>18.10 |
| 42 | (phenyl, 3-NO₂) | A | 74.4 | dimethylformamide, water | 198–202.5 | 250(16,500) | C,62.33<br>H, 3.92<br>N,18.17 | 62.27<br>4.00<br>18.37 |
| 43 | (phenyl, 3,5-(NO₂)₂) | A | 87.41 | dimethylformamide, water | 254–256 | c | C,54.40<br>H, 3.14<br>N,19.82 | 54.35<br>3.31<br>19.82 |
| 44 | (phenyl, 4-C≡N) | A | 60.87 | dimethylformamide, water | 219–220.5 | 234(1,500) | C,70.82<br>H, 4.20<br>N,19.49 | 70.14<br>4.45<br>19.15 |
| 45 | (phenyl, 4-F) | B | 56.8 | benzene | 205–208 | 229(18,500) | C,68.32<br>H, 4.30<br>N,14.94 | 67.86<br>4.02<br>15.17 |
| 46 | (phenyl, 2,3-F) | A | 53.2ª | dimethylformamide, water | 93–96 | 260(10,100) | C,66.20<br>H, 4.51<br>N,14.47 | 65.96<br>4.37<br>14.40 |

TABLE II-continued 1-(2-Arylamidophenyl)imidazoles

| No. | Ar | Isolation Method | % Yield | Crystallization Solvent | m.p., °C. | λmax.(Am) | Analysis Calc'd Found |
|---|---|---|---|---|---|---|---|
| 47 | 4-Br-C₆H₄- | A | b | dimethylformamide | 189–190.5 | 240(22,100) | C,56.16 56.03<br>H, 3.53 3.58<br>N,12.28 12.51 |
| 48 | 2-Br-C₆H₄- | A | 40.1 | dimethylformamide, water | 199–201.5 | 258(20,100) | C,56.16 55.84<br>H, 3.53 3.58<br>N,12.28 12.48 |
| 49 | 2-Cl-C₆H₄- | A | 38.7 | dimethylformamide, ethanol | 201–203 | 261(16,700) | C,64.54 64.70<br>H, 4.06 4.05<br>N,14.11 13.95 |
| 50 | 3-Cl-C₆H₄- | B | 68.5 | ethanol | 144–146 | c | C,64.54 64.82<br>H, 4.06 3.92<br>N,14.11 14.59 |
| 51 | 4-Cl-C₆H₄- | A | 59.7 | ethanol | 167–170 | 240(26,410) | C,64.54 64.41<br>H, 4.06 3.94<br>N,14.11 13.92 |
| 52 | 2,4-Cl₂-C₆H₃- | A | 26.6 | dimethylformamide, water | 210–212 | 265(21,000) | C,57.85 58.05<br>H, 3.34 3.46<br>N,12.65 13.08 |
| 53 | 3,4-Cl₂-C₆H₃- | A | 61.2 | dimethylformamide, water | 180.5–183 | 235(22,100) | C,57.85 57.65<br>H, 3.34 3.51<br>N,12.65 12.93 |
| 54 | 4-I-C₆H₄- | A | 42.9 | ethanol | 186.5–189 | 255(28,480) | C,49.38 49.22<br>H, 3.11 3.15<br>N,10.80 10.85<br>I,32.61 32.89 |
| 55 | 4-CH₃O-C₆H₄- | B | 58.6 | isopropanol | 146–151 | 263(20,400) | C,69.61 69.01<br>H, 5.15 5.14<br>N,14.33 14.36 |
| 56 | 3-CH₃O-C₆H₄- | B | 83.2 | dimethylformamide, water | 171–173 | 281(5,100) | C,69.61 69.27<br>H, 5.15 5.02<br>N,14.33 14.28 |

4,172,947

TABLE II-continued

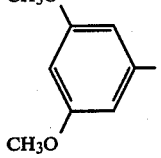

1-(2-Arylamidophenyl)imidazoles

| No. | Ar | Isolation Method | % Yield | Crystallization Solvent | m.p., °C. | λmax.(Am) | Analysis Calc'd | Found |
|---|---|---|---|---|---|---|---|---|
| 57 | 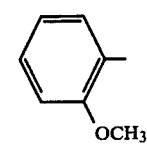 | B | 61.2 | benzene | 130–132.5 | 244,sh(12,300) | C,66.86<br>H, 5.30<br>N,13.00 | 66.97<br>5.02<br>13.54 |
| 58 |  | C | 29.79 | dimethylformamide, water | 133–136.5 | 281(15,410) | C,69.61<br>H, 5.15<br>N,14.33 | 69.10<br>5.08<br>14.18 |
| 59 | 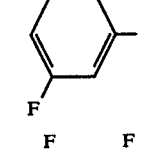 | B | 18.26 | dimethylformamide, water | 164.5–166.5 c | | C,56.16<br>H, 3.54<br>N,12.28 | 55.65<br>3.51<br>12.37 |
| 60 | 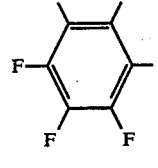 | A | 51.07 | isopropanol | 142.5–145.5 | 223(14,420) | C,68.32<br>H, 4.30<br>N,14.94 | 67.79<br>4.36<br>14.58 |
| 61 | 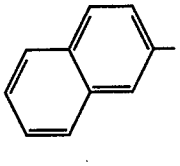 | B | 15.68 | isopropanol-ethanol | 203.5–205 | 258(18,840) | C,54.40<br>H, 2.28<br>N,11.90 | 53.78<br>2.30<br>12.16 |
| 62 | 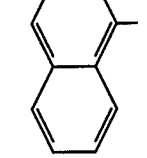 | A | 46.9 | isopropanol | 165.5–167.5 | 237(53,900) | C,76.66<br>H, 4.83<br>N,13.41 | 76.29<br>4.84<br>13.27 |
| 63 | 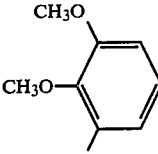 | A | 36.78 | isopropanol-dimethylformamide | 175–177 | 289(6,940) | C,76.66<br>H, 4.82<br>N,13.41 | 76.68<br>4.75<br>12.01 |
| 190 |  | B | 38.80 | benzene | 156–157.5 | 268(13,800) | C,64.58<br>H, 5.42<br>N,11.89 | 64.58<br>5.39<br>12.02 |

TABLE II-continued 1-(2-Arylamidophenyl)imidazoles

| No. | Ar | Isolation Method | % Yield | Crystallization Solvent | m.p., °C. | λmax.(Am) | Analysis Calc'd | Found |
|---|---|---|---|---|---|---|---|---|
| 117 | CH₃O-(aryl)-OCH₃ | A | 45.8 | ethanol | 134–136.5 | 273(14,900) | C,66.86<br>H, 5.30<br>N,13.00 | 66.88<br>5.37<br>12.68 |

Notes:
<sup>a</sup>isolated as hemihydrate.
<sup>b</sup>partial loss prevented yield determination.
<sup>c</sup>Compound absorbed too low for significant U.V.

Alkyl-2-(1-imidazolyl)phenylureylenes (Table III) were prepared by the reaction of equimolar amounts of the aminophenylimidazole and the appropriate isocyanate in toluene solution at steam bath temperatures during two or three hours. Upon cooling, the crude product was collected by filtration and treated by one of the following methods: (A) direct crystallization from the appropriate solvent or (B) dissolved in hot dimethylformamide and precipitated with water followed by crystallization.

TABLE III

Alkyl-2-(1-imidazolyl)phenylureylenes

| No. | R | Isolation Method | % Yield | Crystallization Solvent | m.p., °C. | λmax.(Am) | Analysis Calc'd | Found |
|---|---|---|---|---|---|---|---|---|
| 64 | CH₃— | A | 41.6 | ethanol | 194–196 | 240(15,500) | C,61.60<br>H, 5.59<br>N,25.91 | 61.22<br>5.48<br>26.11 |
| 65 | CH₃CH₂— | B | 27.3 | trichloroethylene | 173–175 | 278(1,200)<br>242(12,700) | C,62.59<br>H, 6.13<br>N,24.33 | 62.21<br>6.04<br>24.32 |
| 66 | CH₃CH₂CH₂— | B | 49.3 | trichloroethylene | 139–141 | 279(1,200)<br>240(12,800) | C,63.92<br>H, 6.60<br>N,22.93 | 63.75<br>6.56<br>23.00 |
| 67 | CH₃CH₂CH₂CH₂— | B | 35.6 | isopropanol | 115–116.5 | 278(14,00)<br>241(15,000) | C,65.00<br>H, 7.02<br>N,21.69 | 64.84<br>7.00<br>21.78 |
| 68 | cyclohexyl-S | A | 50.64 | dimethylformamide, water | 164–166 | 241(12,200) | C,67.58<br>H, 7.09<br>N,19.70 | 67.60<br>7.08<br>19.44 |

Aryl-2-(1-imidazolyl)phenylureylenes (Table IV) were prepared by reacting equimolar amounts of the aminophenylimidazole and the appropriate arylisocyanate in dry toluene during three hours at steam bath temperatures. The reaction mixture was cooled and the crude product was separated by filtration, and washed with ether and crystallized from the indicated solvent.

TABLE IV

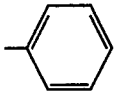

| No. | Ar | % Yield | Recrystallization Solvent | m.p. °C. | λmax.(Am) | Analysis Calc'd | Found |
|-----|----|---------|---------------------------|----------|-----------|-----------------|-------|
| 69 | 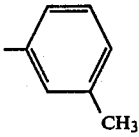 | 64.6 | ethanol | 210–203 | 256(27,640) | C,69.05 H, 5.07 N,20.13 | 69.143 5.15 20.16 |
| 70 | 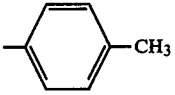 (CH₃) | 76.9 | dimethylformamide-water | 203.5–207.5 | 258(23,400) | C,69.84 H, 5.52 N,19.17 | 69.85 5.47 19.28 |
| 71 | 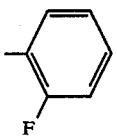 (CH₃) | 76.9 | ethanol | 182–183.5 | 256(25,800) | C,69.84 H, 5.52 N,19.17 | 69.97 5.35 19.12 |
| 72 | 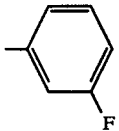 (F) | 78.8 | dimethylformamide-water | 202.5–203.5 | 251(25,500) | C,64.86 H, 4.42 N,18.91 | 64.77 4.40 19.16 |
| 73 | (F) | 61.9 | dimethylformamide-water | 201–202 | 253(26,000) | C,64.86 H, 4.42 N,18.97 | 64.47 4.40 19.24 |
| 74 |  (F) | 65.8 | dimethylformamide-water | 220–222 | 251(23,100) | C,64.86 H, 4.42 N,18.97 | 64.56 4.41 19.14 |
| 75 | 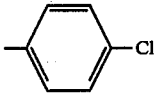 (Cl) | 76.7 | dimethylformamide-water | 204–206 | 258(30,900) | C,61.45 H, 4.19 N,17.91 | 61.57 4.12 18.26 |
| 76 | 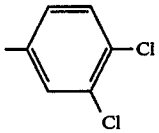 (Cl, Cl) | 58.1 | dimethylformamide-water | 244–245.5 | 260(32,900) | C,55.35 H, 3.48 N,16.14 | 54.93 3.47 16.25 |
| 77 | 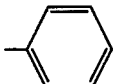 (Br) | 70.0 | dimethylformamide-water | 180.5–182.5 | 252(23,000) | C,53.80 H, 3.76 N,15.68 | 53.88 3.78 15.66 |
| 78 | 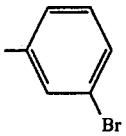 (Br) | 75.2 | dimethylformamide-water | 218–219.5 | 258(28,600) | C,53.80 H, 3.67 N,15.68 | 53.71 3.66 15.35 |
| 79 | 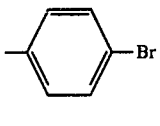 (Br) | 53.1 | methanol | 227–230.5 | 260(27,700) | C,53.80 H, 3.67 N,15.68 | 52.08 3.56 15.12 |

TABLE IV-continued

| No. | Ar | % Yield | Recrystallization Solvent | m.p. °C. | λmax.(Am) | Analysis Calc'd | Found |
|---|---|---|---|---|---|---|---|
| 80 | 4-I-C6H4- | 83.2 | dimethylformamide-water | 201-202 | 253(26,000) | C,64.86<br>H, 4.42<br>N,18.97 | 64.47<br>4.40<br>19.24 |
| 81 | 2-CH3-C6H4- | 57.79 | dimethylformamide-water | 167-170 | 250(20,710) | C,69.84<br>H, 5.52<br>N,19.17 | 70.10<br>5.57<br>18.60 |
| 82 | 4-CF3-C6H4- | 77.4 | dimethylformamide-water | 216.5-218.5 | 256(31,010) | C,58.96<br>H, 3.78<br>N,16.18 | 58.86<br>3.81<br>15.79 |
| 83 | 3,4-(CH3)2-C6H3- | 78.9 | dimethylformamide-water | 212-215 | 260(27,580) | C,70.57<br>H, 5.92<br>N,18.29 | 70.30<br>5.83<br>18.00 |
| 84 | 4-CH2CH3-C6H4- | 76.6 | dimethylformamide-water | 185-188 | 258(29,590) | C,70.57<br>H, 5.92<br>N,18.29 | 70.30<br>5.96<br>18.00 |
| 85 | 3-CH2CH3-C6H4- | 76.2 | dimethylformamide-water | 163.5-166 | 258(28,770) | C,70.57<br>H, 5.92<br>N,18.29 | 70.52<br>5.81<br>17.94 |
| 86 | 4-(CH2)3CH3-C6H4- | 67.8 | dimethylformamide-water | 169-172 | 257(29,920) | C,71.83<br>H, 6.63<br>N,16.75 | 71.61<br>6.56<br>16.24 |
| 87 | 4-CH(CH3)2-C6H4- | 80.6 | dimethylformamide-water | 206-209 | 282(27,620) | C,71.23<br>H, 6.29<br>N,17.49 | 71.12<br>6.12<br>17.24 |
| 88 | 2-CH3O-C6H4- | 69.0 | dimethylformamide-water | 204.5-206 | 285(10,630) | C,66.22<br>H, 5.23<br>N,18.17 | 65.96<br>5.15<br>18.15 |
| 89 | 3-OCH3-C6H4- | 84.0 | dimethylformamide-water | 188 | 252(24,510) | C,66.22<br>H, 5.23<br>N,18.17 | 65.83<br>5.13<br>18.02 |
| 90 | 4-OCH3-C6H4- | 81.9 | dimethylformamide-water | 200-202 | 260(24,560) | C,66.22<br>H, 5.23<br>N,18.17 | 65.61<br>5.14<br>17.98 |

TABLE IV-continued

Reaction scheme: 2-(imidazol-1-yl)aniline + → 2-(imidazol-1-yl)phenyl-NHC(O)NHAr

| No. | Ar | % Yield | Recrystallization Solvent | m.p. °C. | λmax.(Am) | Analysis Calc'd | Found |
|---|---|---|---|---|---|---|---|
| 91 | 4-OCH₂CH₃-C₆H₄ | 80.9 | dimethylformamide-water | 190.5–193 | 259(27,180) | C,67.07 H, 5.63 N,17.38 | 66.80 5.62 17.16 |
| 92 | 4-O(CH₂)₃CH₃-C₆H₄ | 79.5 | dimethylformamide-water | 178–179.5 | 258(26,490) | C,68.55 H, 6.33 N,15.99 | 68.68 6.34 15.62 |
| 93 | 4-(C₆H₅O)-C₆H₄ | 64.1 | dimethylformamide-water | 202.5–205 | 259(35,850) | C,71.34 H, 4.90 N,15.13 | 71.14 4.93 14.78 |
| 94 | 4-SCH₃-C₆H₄ | 75.1 | dimethylformamide-water | 189–191 | 278(32,130) | C,62.94 H, 4.97 N,17.27 | 62.84 4.86 17.22 |
| 95 | 3-Cl-C₆H₄ | 62.3 | dimethylformamide-water | 211.5–214.5 | 259(30,210) | C,61.45 H, 4.19 N,17.91 | 60.94 4.02 17.79 |
| 96 | 3,5-F₂-C₆H₃ | 75.9 | dimethylformamide-water | 198–210 | 252(25,230) | C,61.44 H, 3.85 N,17.83 | 61.33 3.92 17.98 |
| 97 | 3,5-Cl₂-C₆H₃ | 64.8 | dimethylformamide-water | 232.5–234 | 258(32,380) | C,55.35 H, 3.48 N,16.14 | 55.60 3.50 16.00 |
| 98 | 3-Cl-4-CH₃-C₆H₃ | 70.7 | dimethylformamide-water | 237.5–239 | 258(31,300) | C,62.48 H, 4.63 N,17.15 | 62.79 4.70 17.30 |
| 99 | 3-Cl-4-F-C₆H₃ | 70.0 | dimethylformamide-water | 229–232 | 256(25,630) | C,58.10 H, 3.66 N,16.94 | 57.84 3.56 16.90 |
| 100 | 3-CF₃-4-Cl-C₆H₃ | 57.6 | dimethylformamide-water | 239.5–242.2 | 261(37,430) | C,53.63 H, 3.18 N,14.71 | 53.89 3.05 14.41 |
| 101 | 3-CF₃-5-Cl-C₆H₃ | 50.7 | dimethylformamide-water | 190–192 | 255(26,350) | C,53.63 H, 3.18 N,14.71 | 53.70 2.97 14.90 |

TABLE IV-continued

| No. | Ar | % Yield | Recrystallization Solvent | m.p. °C. | λmax.(Am) | Analysis Calc'd | Found |
|---|---|---|---|---|---|---|---|
| 102 | —C₆H₄-NO₂ (4-NO₂) | 42.7 | dimethylformamide-water | 202–205 | 375(4,200) 253(32,970) | C,59.44 H, 4.05 N,21.66 | 59.40 4.10 21.44 |
| 103 | —C₆H₄-NO₂ (2-NO₂) | 44.2 | dimethylformamide-water | 237.5–239.5 | 342(1,800) 264(46,530) | C,59.44 H, 4.05 N,21.66 | 59.16 4.10 21.31 |
| 104 | —C₆H₄-NO₂ | 52.3 | dimethylformamide-water | >257(Dec.) | 330(20,010) | C,59.44 H, 4.05 N,21.66 | 59.01 3.97 21.07 |
| 105 | —C₆H₃(Cl)(NO₂) | 35.4 | dimethylformamide-water | 256.5–258 | 257(33,080) | C,53.72 H, 3.38 N,19.57 | 53.72 3.31 19.63 |
| 106 | —C₆H₃(CH₃)(NO₂) | 57.1 | dimethylformamide-water | 254–256 (Dec.) | 256(36,930) | C,60.53 H, 4.48 N,20.76 | 60.26 4.34 20.68 |
| 107 | —C₆H₄-C≡N | 47.3 | dimethylformamide-water | 244 | 290(57,510) | C,67.32 H, 4.32 N,23.09 | 67.88 4.13 21.37 |
| 108 | —C₆H₄-C(O)OCH₃ | 33.8 | dimethylformamide-water | 227.5–229.5 | 297(32,710) | C,67.48 H, 5.03 N,17.49 | 67.49 5.05 17.07 |
| 191 | —naphthyl | 35.2 | dimethylformamide-water | 233–236 | 284(16,710) | C,73.15 H, 4.91 N,17.06 | 72.70 4.97 16.63 |
| 192 | —C₆H₃(NO₂)(F) | 25.2 | dimethylformamide-methanol-water | 231–232 | 252(32,920) | C,56.31 H, 3.55 N,20.52 | 54.13 3.50 20.21 |

4-Alkylimidazo[1,2-a]quinoxalines (Table V) were prepared by refluxing the appropriate amide (Table I, compounds 1–33) with phosphorous oxychloride in excess pyridine during one hour. The reaction mixture was stirred into water and sufficient azeotrope removed to form a viscous residue which was dissolved in chloroform, dried over MgSO₄, and chromatographed through an alumina column. The chloroform was evaporated and the product crystallized from the indicated solvent.

TABLE V

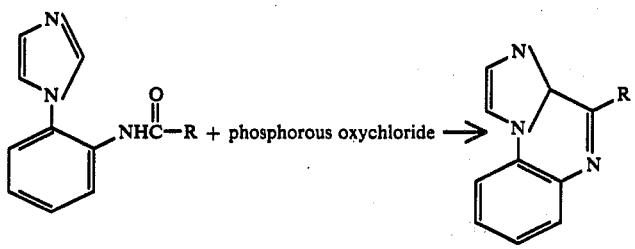

4-alkylimidazo[1,2-a] quinoxalines

| No. | R | % Yield | Recrystallization Solvent | m.p. °C. | λmax. (Am) | Analysis Calc'd | Found |
|---|---|---|---|---|---|---|---|
| 109 | H—[a] | 63.3 | sublimed | 120 | 316(10,900) | | |
| 110 | CH₃— | 13.3 | isopropyl ether | 134–135 | 312(11,200) | C, 72.11 | 72.18 |
| | | | | | | H, 4.95 | 4.89 |
| | | | | | | N, 22.93 | 23.01 |
| 111 | CH₃CH₂— | 37.6 | hexane | 114–115 | 311(10,500) | C, 73.07 | 72.85 |
| | | | | | | H, 5.62 | 5.83 |
| | | | | | | N, 21.30 | 21.29 |
| 112 | CH₃CH₂CH₂— | 14.3 | hexane | 110–111 | 314(10,900) | C, 73.91 | 73.99 |
| | | | | | | H, 6.20 | 6.13 |
| | | | | | | N, 19.89 | 19.94 |
| 113 | CH₃(CH₂)₃— | 17.6 | hexane | 92–93 | 324( 8,000) | C, 74.64 | 74.34 |
| | | | | | | H, 6.70 | 6.74 |
| | | | | | | N, 18.65 | 18.48 |
| 114 | CH₃(CH₂)₄— | 29.2 | b. | 63–65 | 314(11,300) | C, 75.28 | 75.13 |
| | | | | | | H, 7.16 | 7.39 |
| | | | | | | N, 17.56 | 17.43 |
| 115 | CH₃(CH₂)₅— | 10.7 | b. | 43–45 | 313(10,800) | C, 75.86 | 76.03 |
| | | | | | | H, 7.56 | 7.63 |
| | | | | | | N, 16.59 | 16.40 |
| 116 | CH₃(CH₂)₆— | 8.0 | c. | 54–57 | 313( 9,400) | C, 76.37 | 75.84 |
| | | | | | | H, 7.92 | 7.77 |
| | | | | | | N, 15.72 | 16.43 |
| 117 | CH₃(CH₂)₇— | 26.3 | isopropyl ether | 65–66 | 311(11,600) | C, 76.83 | 76.97 |
| | | | | | | H, 8.24 | 8.20 |
| | | | | | | N, 14.93 | 14.89 |
| 118 | CH₃(CH₂)₈— | 9.5 | ethyl ether-hexane | 55–57 | 307(12,500) | C, 77.25 | 77.04 |
| | | | | | | H, 8.53 | 8.36 |
| | | | | | | N, 14.22 | 14.52 |
| 119 | CH₃(CH₂)₁₄— | 24.3 | isopropyl ether | 73–75 | 313(11,300) | C, 79.11 | 79.03 |
| | | | | | | H, 9.82 | 10.02 |
| | | | | | | N, 11.07 | 10.88 |
| 120 | CH₃(CH₂)₁₆— | 13.7 | isopropyl ether | 79–81 | 311(11,300) | C, 79.11 | 79.54 |
| | | | | | | H, 10.14 | 10.12 |
| | | | | | | N, 10.31 | 10.34 |
| 121 | (CH₃)₂CHCH₂— | 12.6 | hexanes | 52–55 | 314(11,700) | C, 74.64 | 74.92 |
| | | | | | | H, 6.71 | 6.81 |
| | | | | | | N, 18.65 | 18.74 |
| 122 | CF₃— | 50.7 | isopropyl ether-chloroform | 184–187 | 328(10,800) | C, 55.70 | 55.94 |
| | | | | | | H, 2.55 | 2.49 |
| | | | | | | N, 17.72 | 17.64 |
| 123 | CH₂=CH(CH₂)₈— | 9.8 | hexanes | 40–42 | 309(13,100) | C, 78.14 | 77.92 |
| | | | | | | H, 8.20 | 7.98 |
| | | | | | | N, 13.67 | 13.96 |
| 124 | C₆H₅—CH₂— | 16.7 | ethanol | 140.5–142 | 312(13,100) | C, 78.74 | 78.59 |
| | | | | | | H, 5.05 | 5.20 |
| | | | | | | N, 16.20 | 16.10 |
| 125 | CH₃OCH₂— | 3.1 | toluene-hexane | 96–5–97.5 | 312(10,600) | C, 67.59 | 67.04 |
| | | | | | | H, 5.20 | 5.17 |
| | | | | | | N, 19.71 | 19.93 |
| 126 | C₆H₅—O—CH₂— | 14.5 | ethanol | 146.5–148.5 | 314(10,400) | C, 74.17 | 74.28 |
| | | | | | | H, 4.76 | 4.61 |
| | | | | | | N, 15.26 | 16.01 |
| 127 | C₆H₅—CH=CH— | 37.2 | benzene | 164–167 | 286(10,500) | C, 79.68 | 80.38 |
| | | | | | | H, 4.83 | 4.91 |
| | | | | | | N, 15.49 | 15.12 |
| 128 | cyclobutyl— | 17.9 | hexane | 106.5–107.5 | 310(11,500) | C, 75.31 | 75.32 |
| | | | | | | H, 5.87 | 5.84 |
| | | | | | | N, 18.82 | 18.75 |
| 129 | cyclohexyl— | 2.0 | hexane | 119–120.5 | 311(11,400) | C, 76.46 | 76.65 |
| | | | | | | H, 6.82 | 6.76 |
| | | | | | | N, 16.72 | 16.58 |

TABLE V-continued

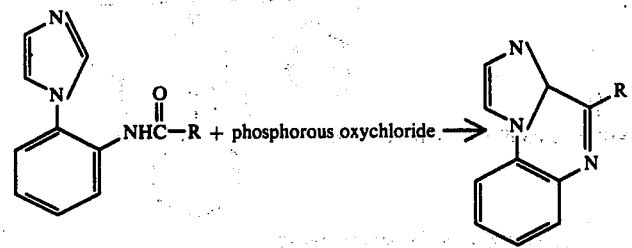

4-alkylimidazo[1,2-a] quinoxalines

| No. | R | % Yield | Recrystallization Solvent | m.p. °C. | λmax. (Am) | Analysis Calc'd | Found |
|---|---|---|---|---|---|---|---|
| 130 | (cyclohexenyl) | 0.8 | isopropyl ether | 133–135 | 312(11,700) | C, 77.39 H, 5.68 N, 16.92 | 77.20 6.13 16.76 |

Notes:
a. A. M. Siminov and I. G. Urykina, Khim. Geterot. Soedin., 7,570(1971) report this compound has an mp of 124° with λ$_{max}^{MeOH}$ (Am) = 315 (10,700).
b. Purified by sublimation at 90°/0.15 mm Pressure.
c. Purified by distillation at 174–184°/0.40 mm P.

4-Arylimidazo[1,2-a]quinoxalines (Table VI) were prepared and isolated according to the general method described for the 4-alkylimidazo[1,2-a]quinoxalines, except as noted in Table VI.

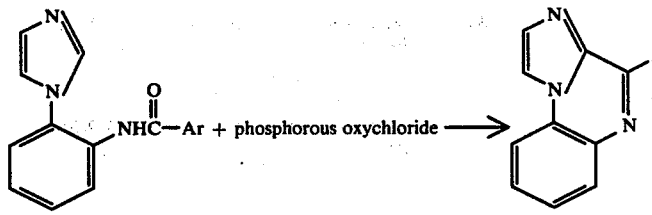

4-Arylimidazo{1,2-a}quinoxalines

| No. | Ar | % Yield | Crystallization Solvent | m.p. °C. | λmax. (Am) | Analysis Calc'd | Found |
|---|---|---|---|---|---|---|---|
| 131 | phenyl a. | 34.8 | benzene | 145–147 | 328(14,100) | C, 78.35 H, 4.52 N, 17.13 | 78.70 4.38 16.90 |
| 132 | 2-CH₃-phenyl | 37.2 | toluene-isopropanol | 149–150.5 | 334(22,650) | C, 78.74 H, 5.05 N, 16.20 | 78.89 5.08 16.27 |
| 133 | 3-CH₃-phenyl | 35.9 | isopropanol-isopropyl ether | 112–114 | 329(15,400) | C, 78.74 H, 5.05 N, 16.20 | 78.53 5.19 16.20 |
| 134 | 4-CH₃-phenyl | 47.1 | isopropanol | 119–120 | 329(18,100) | C, 78.74 H, 5.05 N, 16.20 | 78.32 4.73 15.93 |
| 135 | biphenyl | 37.8 | isopropanol | 136–137 | 331(27,780) | C, 82.22 H, 4.70 N, 13.07 | 82.06 4.38 12.89 |
| 136 | 3-CF₃-phenyl | 47.0 | isooctane | 112–113 | 332(10,411) | C, 65.18 H, 3.22 N, 13.41 | 65.03 3.10 13.62 |
| 137 | 4-(CH₃)₃-phenyl | 56.7 | hexanes | 105–107 | 329(20,354) | C, 79.70 H, 6.35 N, 13.94 | 79.59 6.58 13.84 |
| 138 | 4-CH₃O-phenyl | 37.2 | isopropanol-toluene | 149–150.5 | 334(22,650) | C, 74.17 H, 4.76 N, 15.26 | 74.18 4.79 15.33 |
| 139 | 3,5-(CH₃O)₂-phenyl | 51.5 | isopropanol | 136–138 | 329(16,600) | C, 70.81 H, 4.95 N, 13.76 | 70.61 5.06 13.56 |

-continued

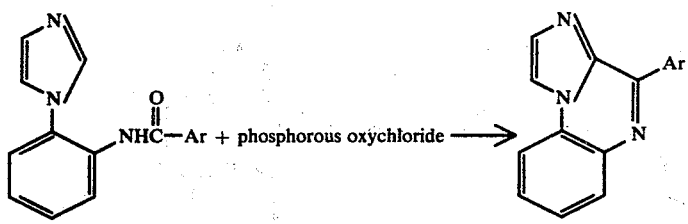

4-Arylimidazo[1,2-a]quinoxalines

| No. | Ar | % Yield | Crystallization Solvent | m.p. °C. | λmax. (Am) | Analysis Calc'd | Found |
|---|---|---|---|---|---|---|---|
| 140 | Cl—⌬— | 31.5 | ethanol | 173–175 | 328(16,280) | C, 68.70<br>H, 3.60<br>N, 15.02 | 69.06<br>3.28<br>15.08 |
| 141 | ⌬ (Cl meta) | 6.8 | benzene-hexanes | 166–168 | 331(10,300) | C, 68.70<br>H, 3.60<br>N, 15.02 | 68.77<br>3.48<br>14.87 |
| 142 | ⌬ (Cl) | 35.2 | isopropanol | 133–134 | 330(14,000) | C, 68.70<br>H, 3.60<br>N, 15.02 | 68.43<br>3.45<br>14.89 |
| 143 | Cl—⌬—(Cl) | 61.9 | toluene | 215–217.5 | 333(16,530) | C, 61.16<br>H, 2.89<br>N, 13.37 | 60.94<br>2.82<br>13.50 |
| 144 | Cl—⌬—(Cl) | 3.4 | carbon tetrachloride | 168–170 | 321(13,030) | C, 61.17<br>H, 2.89<br>N, 13.37 | 60.61<br>2.85<br>13.57 |
| 145 | ⌬—Br | 24.1 | dimethylformamide-water | 161.5–164.5 | 319(10,200) | C, 59.28<br>H, 3.11<br>N, 12.96 | 58.75<br>3.03<br>12.90 |
| 146 | Br—⌬— | 13.4 | dimethylformamide-water | 172 | 329(12,900) | C, 59.28<br>H, 3.11<br>N, 12.96 | 59.34<br>3.13<br>13.23 |
| 147 | F—⌬— | 39.1 | isopropanol | 183–185 | 328(14,500) | C, 72.90<br>H, 3.83<br>N, 15.96 | 73.00<br>4.06<br>15.77 |
| 148 | ⌬—COOH (b.) | 15.0 | ethanol | 190–192 | 222(48,000) | C, 70.58<br>H, 3.83<br>N, 14.52 | 70.54<br>3.71<br>14.67 |
| 149 | NHC—⌬— | 53.3 | dimethylformamide-water | 257.5–259.5 | 335(14,900) | C, 75.54<br>H, 3.73<br>N, 20.73 | 75.15<br>3.85<br>20.66 |
| 150 | ⌬—NO₂ | 59.8 | 2-ethoxyethanol | 220.5–222.5 | 333(13,850) | C, 66.20<br>H, 3.47<br>N, 19.30 | 66.10<br>3.48<br>19.53 |
| 151 | NO₂—⌬— | 40.3 | toluene | 249–252 | 346(15,269) | C, 66.20<br>H, 3.47<br>N, 19.30 | 66.10<br>3.44<br>19.28 |
| 152 | NO₂—⌬—NO₂ | 52.5 | dimethylformamide | 283–285 | 340(10,880) | C, 57.30<br>H, 2.71<br>N, 20.89 | 57.08<br>2.74<br>21.11 |
| 153 | NH₂—⌬— (c.) | 75.7 | dimethylformamide-water | 198–199.5 | 369(23,470) | C, 73.83<br>H, 4.65<br>N, 21.53 | 73.48<br>4.69<br>21.54 |
| 154 | ⌬—NH₂ (c.) | 61.9 | dimethylformamide-water | 130–133 | 326(14,830) | C, 73.83<br>H, 4.65<br>N, 21.53 | 73.56<br>4.78<br>21.69 |
| 155 | CH₃CNH—⌬— · ½H₂O (d.) | 58.0 | ethylacetate-hexane | 214–217 | 342(27,700) | C, 68.88<br>H, 4.66<br>N, 17.85 | 68.46<br>4.99<br>17.76 |

-continued

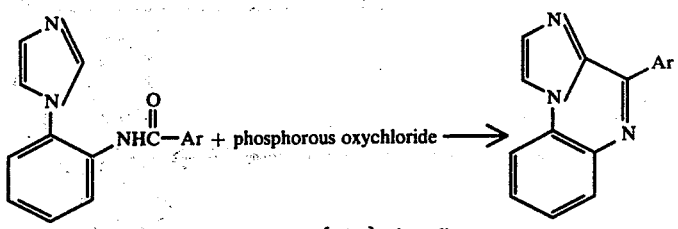

4-Arylimidazo{1,2-a}quinoxalines

| No. | Ar | % Yield | Crystallization Solvent | m.p. °C. | λmax. (Am) | Analysis Calc'd | Found |
|---|---|---|---|---|---|---|---|
| 156 | Cl—C₆H₄—C(O)—N(H)—C₆H₄— d. ½ H₂O | 13.9 | dimethylformide-water | 237.5–240 | 345(32,350) | C, 68.24<br>H, 4.66<br>N, 17.86 | 68.64<br>4.99<br>17.76 |
| 173 | 2-F-C₆H₄— | 32.3 | ethanol | 155–157 | 345(32,350) | C, 68.24<br>H, 4.66<br>N, 17.86 | 68.46<br>4.99<br>17.76 |
| 157 | 3-Br-C₆H₄— | 56.6 | dimethylformamide-water | 134.5–136 | 332(14,260) | C, 59.28<br>H, 3.11<br>N, 12.96 | 59.25<br>3.04<br>13.11 |
| 158 | 3-F-C₆H₄— | 47.5 | dimethylformamide-water | 132.5–134 | 330(13,970) | C, 72.99<br>H, 3.83<br>N, 15.96 | 73.00<br>3.79<br>15.84 |
| 159 | 3-CH₃O-C₆H₄— | 52.7 | ethanol | 113–114.5 | 329(16,500) | C, 74.17<br>H, 4.76<br>N, 15.26 | 74.09<br>4.71<br>15.05 |
| 160 | 1-naphthyl | 10.62 | chloroform | 159–161.5 | 323(15,290) | C, 81.34<br>H, 4.43<br>N, 14.23 | 81.29<br>4.41<br>14.22 |
| 161 | 2-naphthyl | 43.2 | benzene | 154.5–156.5 | 340(21,800) | C, 81.34<br>H, 4.44<br>N, 14.23 | 81.19<br>4.57<br>13.92 |
| 162 | HO—C₆H₄— e. H₂O | 25.4 | isopropanol | 210–215 | 343(23,800) | C, 68.81<br>H, 4.69<br>N, 15.04 | 68.99<br>4.63<br>14.92 |
| 163 | CH₃CO-O—C₆H₄— f. | 84.2 | ethanol | 158–160 | 333(14,950) | C, 71.28<br>H, 4.32<br>N, 13.85 | 71.31<br>4.44<br>13.85 |
| 164 | CH₃(CH₂)₂CO-O—C₆H₄— f. | 80.3 | ethanol | 116–118 | 335(15,100) | C, 72.49<br>H, 5.17<br>N, 12.68 | 72.38<br>5.42<br>12.36 |
| 165 | CH₃(CH₂)₈CO-O—C₆H₄— f. | 62.6 | ethanol | 90.5–93.5 | 335(15,100) | C 75.15<br>H, 7.03<br>N, 10.11 | 74.87<br>7.16<br>9.94 |
| 166 | CH₃(CH₂)₁₄CNH—C₆H₄— d. ¼ H₂O | 45.85 | chloroform | 154–155.5 | 344(27,240) | C, 76.38<br>H, 8.51<br>N, 11.14 | 76.58<br>8.35<br>10.81 |
| 193 | EtO—C₆H₄— g. | 29.80 | ethanol | 150–152 | 342(22,900) | C, 74.72<br>H, 5.23<br>N, 14.52 | 74.37<br>5.17<br>14.33 |
| 196 | I—C₆H₄— | 8.2 | dimethylformamide-water | 178–181 | 330(27,300) | C, 51.77<br>H, 2.72<br>N 11.32 | 51.89<br>2.68<br>11.46 |
| 219 | C₆H₅—O—C₆H₄— g. | 37.1 | toluene | 151.5–153.5 | 333(21,000) | C, 78.32<br>H, 4.48<br>N, 12.45 | 78.32<br>4.63<br>12.22 |
| 220 | CH₃O—C₆H₄—O—C₆H₄— g. | 35.1 | benzene | 151.5–153.5 | 337(22,200) | C, 75.19<br>H, 4.66<br>N, 11.44 | 75.42<br>4.58<br>11.46 |
| 221 | HO—C₆H₄—O—C₆H₄— h. ¼ H₂O | 33.3 | ethanol-water | >300° | 343(22,700) | C, 72.92<br>H, 4.65<br>N, 11.60 | 73.21<br>4.31<br>11.74 |
| 222 | CH₃(CH₂)₃S—C₆H₄— g. | 28.2 | ethanol | 83–85 | 348(24,600) | C, 72.04<br>H, 5.74<br>N, 12.60 | 71.64<br>5.68<br>12.62 |

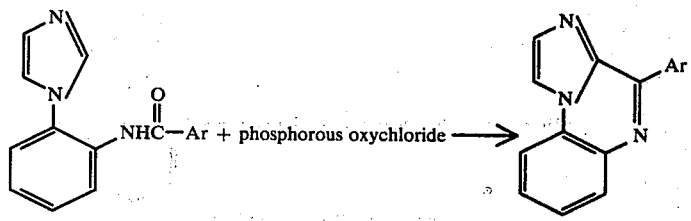

4-Arylimidazo[1,2-a]quinoxalines

| No. | Ar | % Yield | Crystallization Solvent | m.p. °C. | λmax. (Am) | Analysis Calc'd | Found |
|---|---|---|---|---|---|---|---|
| 194 | CH3O, CH3O—, CH3O | 22.6 | toluene | 164–165.5 | 339(19,400) | C, 68.05<br>H, 5.11<br>N, 12.53 | 67.70<br>5.03<br>12.32 |

Notes To Table VI:

a. U.S. Pat. No. 3,887,566 describes this compound as having a m.p. of 154°–157° C.

b. Prepared by refluxing equimolar amounts of the 2-aminophenylimidazole and phthalic anhydride in toluene for one and one-half hours. Upon cooling, the product separated out of solution.

c. Prepared by catalytic hydrogenation with 10% palladium on carbon of a dimethylformamide solution of the nitro analog; crude product precipitated with water. Prepared by treating compound 153 in pyridine with the appropriate acid chloride followed by precipitation with water.

e. Prepared by HI cleavage of compound No. 138.

f. Prepared by treating the lithium salt of compound No. 162 with the appropriate acid chloride in DMF followed by precipitation with water.

g. Prepared by treating compound No. 151 with the appropriate nucleophile according to the method of Kornblum et al, J. Org. Chem., 41, 1560(1976).

h. Prepared by HI cleavage of compound 220.

The 4-Alkylaminoimidazo[1,2-a]quinoxalines (Table VII) were prepared by treating the corresponding alkylureylenes (Table III) with phosphorous oxychloride and pyridine during one-half hour at reflux temperatures. The reaction mixture was poured into cold water and the excess pyridine was removed by azeotropic distillation. The crude product was dissolved in chloroform and pass through an alumina column. After evaporation of the chloroform, the solid was crystallized from the indicated solvent and obtained in the indicated yield.

TABLE VII

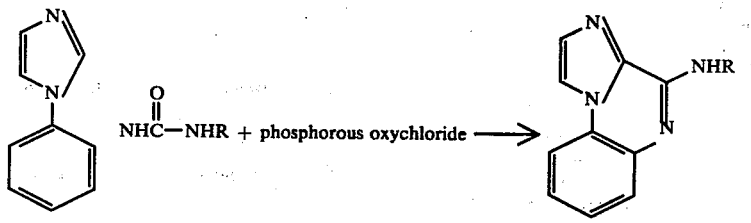

4-Alkylaminoimidazo[1,2-a]quinoxalines

| No. | R | % Yield | Crystallization Solvent | m.p. °C. | λmax. (Am) | Analysis Calc'd | Found |
|---|---|---|---|---|---|---|---|
| 167 | (thianyl) | 4.89 | hexane | 98.5–101.5 | 335(11,700) | C, 72.15<br>H, 6.81<br>N, 21.04 | 72.02<br>6.75<br>20.81 |
| 168 | CH3(CH2)2CH2— | 28.33 | isopropyl ether | 102–104 | 332(11,480) | C, 69.97<br>H, 6.71<br>N, 23.31 | 70.12<br>6.71<br>23.21 |
| 169 | CH3(CH2)2— | 7.5 | isopropyl ether | 72–74 | 317(15,800) | C, 69.00<br>H, 6.24<br>N, 24.76 | 69.14<br>6.35<br>24.60 |

4-arylaminoimidazo[1,2-a]quinoxalines (Table VIII) were prepared by treating the corresponding arylureylenes (Table IV) with an equimolar amount of phosphorus oxychloride in refluxing pyridine during one hour. The cooled reaction mixture was stirred into cold water, and the crude solid which separated was dissolved in chloroform, dried and passed through an alumina column. The chloroform was evaporated and the crude solid was crystallized as indicated in Table VIII.

TABLE VIII

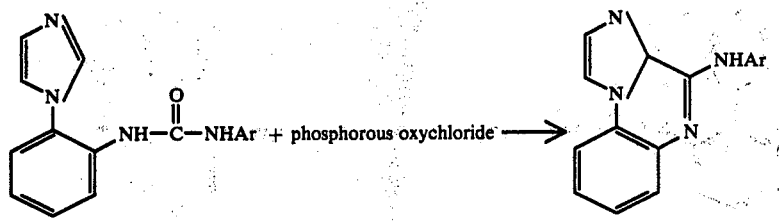

4-Arylaminoimidazo[1,2-a]quinoxalines

| No. | Ar | % Yield | Crystallization Solvent | m.p. °C. | λmax. (Am) | Analysis Calc'd | Found |
|---|---|---|---|---|---|---|---|
| 170 | ⌬ a. | 7.2 | ethanol-water | 120–123 | 304(13,800) | C, 72.57<br>H, 4.76<br>N, 21.16 | 72.67<br>4.71<br>20.88 |
| 171 | CH₃-⌬- | 13.1 | methanol-chloroform | 151 | 334(20,700) | C, 74.43<br>H, 5.14<br>N, 20.42 | 74.16<br>5.06<br>20.09 |
| 172 | ⌬-CH₃ | 11.7 | methanol-chloroform | 153–155 | 330(20,200) | C, 74.43<br>H, 5.14<br>N, 20.42 | 73.23<br>5.26<br>20.02 |
| 174 | Cl-⌬- | 13.6 | methanol-chloroform | 176.5–178 | 330(22,200) | C, 65.26<br>H, 3.75<br>N, 19.02 | 65.04<br>3.77<br>18.91 |
| 175 | Cl,Cl-⌬- | 10.9 | methanol-chloroform | 178.5–180.5 | 344(33,600) | C, 58.38<br>H, 3.06<br>N, 17.02 | 58.15<br>3.06<br>17.09 |
| 176 | I-⌬- | 18.2 | toluene-chloroform | 193.5–195 | 332(4,500) | C, 49.76<br>H, 2.87<br>N, 14.51 | 49.72<br>3.10<br>14.39 |
| 177 | ⌬-Br | 11.5 | ethanol | 196.5–198.5 | 324(16,600) | C, 56.66<br>H, 3.27<br>N, 16.52 | 56.69<br>3.24<br>16.43 |
| 178 | ⌬-Br | 15.0 | methanol-chloroform | 184–185.5 | 329(24,100) | C, 56.66<br>H, 3.27<br>N, 16.52 | 56.26<br>3.20<br>16.54 |
| 179 | Cl-⌬- ½H₂O | 10.52 | dimethylformamide-water | 122–124 | 343(19,600) | C, 63.27<br>H, 3.98<br>N, 18.45 | 62.94<br>4.19<br>18.58 |
| 180 | ⌬-F | 13.0 | ethanol-dimethylformamide | 139 | 339(19,810) | C, 69.05<br>H, 3.98<br>N, 20.13 | 68.88<br>4.02<br>20.13 |
| 181 | ⌬-F | 9.4 | isopropanol | 148.5–149.5 | 343(20,230) | C, 69.05<br>H, 3.98<br>N, 20.13 | 68.92<br>4.00<br>20.14 |
| 182 | F-⌬- | 3.1 | isopropanol | 139.5–141 | 331(18,030) | C, 69.05<br>H, 3.98<br>N, 20.13 | 68.50<br>3.92<br>19.86 |
| 183 | Br-⌬- | 16.58 | dimethylformamide-water | 166–168.5 | 347(21,730) | C, 56.66<br>H, 3.27<br>N, 16.52 | 56.31<br>3.25<br>16.56 |
| 184 | ⌬-OCH₃ | 11.4 | dimethylformamide-water | 207–209 | 366(22,410) | C, 70.33<br>H, 4.86<br>N, 19.30 | 70.61<br>5.11<br>19.11 |
| 185 | ⌬-OCH₃ | 8.3 | dimethylformamide-water | 116.5–117.5 | 335(21,820) | C, 70.33<br>H, 4.86<br>N, 19.30 | 70.16<br>5.28<br>19.31 |
| 186 | CH₃O-⌬- | 14.12 | dimethylformamide-water | 147–149 | 339(18,540) | C, 70.33<br>H, 4.86<br>N, 19.30 | 70.14<br>4.28<br>19.31 |

TABLE VIII-continued

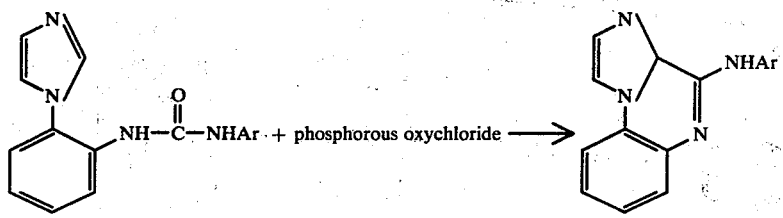

4-Arylaminoimidazo{1,2-a}quinoxalines

| No. | Ar | % Yield | Crystallization Solvent | m.p. °C. | λmax. (Am) | Analysis Calc'd | Found |
|---|---|---|---|---|---|---|---|
| 187 | 2-NO₂-C₆H₄ · ¼ H₂O | 2.0 | isopropanol-dimethyl-formamide | 195–197 | 341(20,370) | C, 60.28 H, 3.95 N, 21.97 | 60.21 3.88 21.63 |
| 188 | 3-NO₂-C₆H₄ | 36.4 | dimethylformamide-water | 241–243.5 | 400(8,960) | C, 62.95 H, 3.63 N, 22.94 | 62.62 3.63 22.68 |
| 189 | 4-NO₂-C₆H₄ | 33.1 | dimethylformamide-water | 323–324.5 | 368(23,670) | C, 62.95 H, 3.63 N, 22.94 | 62.73 3.73 22.81 |
| 195 | 4-PhO-C₆H₄ | 11.61 | dimethylformamide-water | 138.5–141 | 335(22,900) | C, 74.99 H, 4.58 N, 15.90 | 75.02 4.66 75.02 |
| 197 | 2-CH₃-C₆H₄ | 5.52 | dimethylformamide-water | 143–145 | 330(18,000) | C, 74.43 H, 5.15 N, 20.42 | 74.63 5.16 20.09 |
| 198 | 2,4-(CH₃)₂-C₆H₃ | 10.91 | dimethylformamide | 163.5–165.5 | 337(18,800) | C, 74.98 H, 5.59 N, 19.43 | 74.69 5.56 19.43 |
| 199 | 3-CH₃CH₂-C₆H₄ · ¼ H₂O | 15.29 | dimethylformamide-water | 81–83 | 333(20,800) | C, 73.83 H, 5.51 N, 19.13 | 73.87 5.47 18.88 |
| 200 | 4-CH₃CH₂-C₆H₄ · ¼ H₂O | 13.81 | dimethylformamide-water | 124.5–127 | 335(23,200) | C, 73.83 H, 5.51 N, 19.13 | 74.14 5.47 19.02 |
| 201 | 4-CH₃(CH₂)₃-C₆H₄ | 16.96 | isopropanol-water | 89.5–91.5 | 335(21,000) | C, 73.83 H, 5.51 N, 19.13 | 74.14 5.47 19.02 |
| 202 | 2-naphthyl · ¼ H₂O | 11.50 | methanol-chloroform | 187–190 | 342(24,200) | C, 76.29 H, 4.56 N, 17.80 | 76.58 4.52 17.58 |
| 203 | 4-CH₃CH₂O-C₆H₄ · ¼ H₂O | 12.50 | dimethylformamide-water | 120.5–123 | 340(20,300) | C, 68.99 H, 5.15 N, 17.88 | 68.32 5.32 17.61 |
| 204 | 4-CH₃(CH₂)₃O-C₆H₄ · ½ H₂O | 21.39 | dimethylformamide-water | 102.5–107 | 340(19,600) | C, 62.20 H, 3.38 N, 17.07 | 61.56 3.34 17.46 |
| 205 | 4-CH₃S-C₆H₄ · ¼ H₂O | 8.5 | dimethylformamide-water | 90–97 | 341(26,400) | C, 65.68 H, 4.62 N, 18.02 | 65.56 4.57 17.88 |
| 206 | 3-CF₃-C₆H₄ | 21.39 | dimethylformamide-water | 129–130 | 347(20,300) | C, 62.20 H, 3.38 N, 17.07 | 61.56 3.34 17.46 |
| 207 | 4-Cl-3-CF₃-C₆H₃ | 11.49 | dimethylformamide-water | 178.5–179.5 | 324(25,500) | C, 56.29 H, 2.78 N, 15.45 | 55.86 2.72 15.37 |
| 208 | 3-Cl-4-CF₃-C₆H₃ | 7.52 | dimethylformamide-water | 172.5–173.5 | 345(24,900) | C, 56.29 H, 2.78 N, 15.45 | 56.13 2.72 15.35 |

TABLE VIII-continued

NH—C(=O)—NHAr (with imidazole-phenyl) + phosphorous oxychloride → 4-arylaminoimidazo{1,2-a}quinoxaline 4-Arylaminoimidazo{1,2-a}quinoxalines

| No. | Ar | % Yield | Crystallization Solvent | m.p. °C. | λmax. (Am) | Analysis Calc'd | Found |
|---|---|---|---|---|---|---|---|
| 209 | CH$_3$—C$_6$H$_3$—Cl · ¼ H$_2$O | 15.18 | dimethylformamide-water | 170–172 | 332(23,800) | C, 65.18 H, 4.18 N, 17.89 | 65.35 4.15 17.91 |
| 210 | F—C$_6$H$_3$—F | 13.56 | dimethylformamide-water | 171.5–173 | 337(17,300) | C, 64.86 H, 3.40 N, 18.81 | 64.92 3.51 18.91 |
| 211 | Cl—C$_6$H$_3$—Cl · ¼ H$_2$O | 10.78 | dimethylformamide-water | 259.5–261.5 | 342(23,200) | C, 56.82 H, 3.28 N, 16.57 | 56.76 3.07 16.57 |
| 212 | F—C$_6$H$_3$—Cl | 7.22 | dimethylformamide-water | 198–200 | 343(18,400) | C, 61.45 H, 3.22 N, 17.92 | 61.35 3.27 17.81 |
| 213 | F—C$_6$H$_3$—NO$_2$ · ¼ H$_2$O | 3.04 | methanol-chloroform | 229–231 | 341(19,900) | C, 58.63 H, 3.15 N, 21.36 | 58.50 3.06 21.20 |
| 214 | CH$_3$—C$_6$H$_3$—NO$_2$ · ¼ H$_2$O | 4.18 | methanol-chloroform | 168–170 | 344(21,400) | C, 63.06 H, 4.12 N, 21.63 | 62.97 4.08 21.34 |
| 215 | Cl—C$_6$H$_3$—NO$_2$ | 19.43 | dimethylformamide-water | 271–273 | 346(19,600) | C, 56.57 H, 2.97 N, 20.61 | 56.44 2.90 20.51 |
| 216 | N≡C—C$_6$H$_4$— | 5.96 | dimethylformamide-water | 224–226.5 | 349(34,700) | C, 70.48 H, 3.91 N, 24.17 | 70.89 3.94 24.09 |
| 218 | (CH$_3$)$_2$CH—C$_6$H$_4$— | 2.31 | isopropanol | 95–96.5 | — | C, 75.47 H, 6.00 N, 18.53 | 75.08 6.34 18.53 |

Various compounds of this invention display antifungal and anti-yeast activity. Thus, for example, they have been found to be effective against such organisms as *Candida albicans* (ATCC No. 10231), *Candida tropicalis*, *Aspergillus niger* (ATCC No. 16404), *Trichophyton mentagrophytes* (ATCC No. 8757 and 9129), *Trichophyton rubrum* (ATCC No. 10218 and 14001) and *Trichophyton ajelloi*.

The antifungal activity of compounds of this invention indicate their usefulness against dermatomycosis such as tinea capitis, tinea favosa, tinea barbae, tinea corporis, tinea imbricata, tinea cruris, tinea pedis, tinea manus, tinea unquium and various types of candidiasis such as glossitis, stomatitis, chelitis, perlèche, vaginitis and balanitis.

When the compounds of the present invention are used for antifungal medical purposes, they will usually be incorporated in a suitable pharmaceutical carrier. These antifungal preparations may take the form of solutions, lotions, creams, ointments, etc. The quantity of antifungal agent of this invention that will be contained in such preparations may vary somewhat. Ordinarily, however, it will constitute about 0.5% to 10.0% by weight based on the total weight of the preparation.

In Table IX below are listed the antifungal activity of a number of compounds encompassed in the present invention. These were determined by the agar dilution method as described in Chapters 2 and 3 of *Methods in Microbiology*, Vol. 7B, edited by J. R. Norris and D. W. Ribbons, Academic Press, New York, 1972.

TABLE IX

Antifungal Activity
Parts Per Million Inhibitions of
Fungus and Yeast Species

| Compound No. | C. albicans | C. tropicalis | A. niger | T. ajelloi | T. mentagrophytes | T. rubrum |
|---|---|---|---|---|---|---|
| 20 | | | | 100 | 100 | |
| 136 | | | | | 100 | |
| 40 | 100 | 100 | | 100 | 100 | |
| 35 | | | | | 100 | 16 |

TABLE IX-continued

Antifungal Activity
Parts Per Million Inhibitions of
Fungus and Yeast Species

| Compound No. | C. albicans | C. tropicalis | A. niger | T. ajelloi | T. mentagrophytes | T. rubrum |
|---|---|---|---|---|---|---|
| 39 | | | | 100 | 100 | |
| 133 | 100 | 100 | | 8 | 8 | 8 |
| 134 | | | | 100 | 16 | |
| 139 | | | | | 100 | |
| 137 | | | | 100 | 100 | |
| 135 | | | | 100 | 100 | |
| 142 | | | | | 100 | |
| 132 | | | | 100 | 100 | |
| 138 | | | | 100 | 100 | |
| 130 | 100 | 100 | | 100 | 100 | |
| 113 | 100 | 100 | | | 100 | |
| 9 | | | | | 16 | 16 |
| 10 | | | | | 16 | 16 |
| 116 | | | | | 16 | 16 |
| 127 | | | | | 16 | 16 |
| 109 | | | | | 128 | 32 |
| 114 | | | | | 16 | 1 |
| 118 | | | | | 256 | 4 |
| 123 | | | | | | 2 |
| 131 | | | | | 16 | 2 |
| 140 | | | | | | <0.5 |
| 151 | | | | | | 1 |
| 119 | | | | | | 8 |
| 120 | | | | | | 1 |
| 8 | | | | | 8 | 8 |
| 16 | | | | | 4 | 2 |
| 110 | | | 128 | | 128 | 64 |
| 122 | | | | | | 32 |
| 112 | | | | | 128 | 64 |
| 153 | | 100 | | | | |
| 124 | 100 | 100 | | 100 | 100 | 8 |
| 58 | | | | 100 | 100 | 100 |
| 59 | | | | | | 100 |
| 62 | | | | 100 | 100 | 100 |
| 126 | | | | 100 | 100 | 100 |
| 145 | | | | 100 | 100 | 100 |
| 159 | | | | 100 | 100 | 100 |
| 160 | | | | 100 | 100 | 100 |
| 163 | | | | 100 | 100 | 100 |
| 164 | | | | 100 | 100 | 100 |
| 165 | | | | 100 | 100 | 100 |
| 167 | | | | 100 | 100 | 100 |
| 168 | | | | 100 | 100 | 100 |
| 169 | | | | 100 | 100 | 100 |
| 173 | | | | 100 | 100 | 100 |
| 179 | | | | 100 | 100 | 100 |
| 182 | | | | | | 100 |
| 184 | | | | 100 | 100 | 100 |
| 185 | | | | 100 | 100 | 100 |
| 186 | | | | 100 | 100 | 100 |
| 189 | | | | 100 | | 100 |
| 187 | | | | 100 | | 100 |
| 128 | | | | | | 16 |
| 129 | | | | 16 | 16 | 8 |

A number of the compounds encompassed in the present invention have been found to have immunosuppressant action. Of those tested, most of these are of the 4-substituted imidazo[1,2-a]quinoxaline type described in formula I above, although a couple are of the 1-(2-acylaminophenyl)imidazole type shown in formula II. Because they exhibit this activity, they are indicated for use in the treatment of those diseases that the prior art recognizes may be helped by the administration of immunosuppressants. These include such conditions as: glomerulonephritis, serum sickness, organ transplant, rheumatoid arthritis, systemic lupus erythematosis, ulcerative colitis, chronic active hepatitis, multiple sclerosis, heterografts or homografts in burns, psoriatic arthritis, urticaria, respiratory allergies, i.e. asthma, hayfever; scleraclerma, mycosis fungoides, dermatomyositis, psoriasis and contact dermatitis (including poison ivy).

The dosage level for administering the immunosuppressants of the present invention will vary with the particular compound that is to be administered. In general, this will be at about the same level of the prior art immunosuppressants. For the most part, when the present immunosuppressants are administered orally or intraveneously, the daily dose would be in the range of about 0.1 mg. to 15 mg./per kilogram of body weight. When other mode of administration are employed, e.g. depot injections, implants, etc. the dose may be considerably higher i.e. up to about 100 mg./kg of body weight in a single injection.

The immunosuppressant activities of the compounds of this invention were determined via the hemolysin test in mice and by the delayed hypersensitivity test. The hemolysin test used is that described in *Methods in Immunology*, edited by D. H. Campbell et al, W. A. Benjamin, New York 1963 pages 172-175, and measured humeral or antibody response. The delayed hypersensitivity test measures the effect of a test compound on the ability of a subject mouse to mount a cell-mediated immune response to the antigen, Mycobacterium tuberculosis H37Ra. The mouse is sensitized to the antigen by subcutaneous administration in the base of the tail. The development of the delayed hypersensitivity response may be measured at any time beginning six days after sensitization but is usually done on the ninth day as follows: The right hind paw is injected with purified protein derivative (tuberculin) while the left hind paw (control) receives physiological saline. Both paw volumes are measured after twenty-four hours and significant increase in the volume of the right hind paw is taken as a measure of an effective delayed hypersensitivity response. All compounds were administered by the subcutaneous route.

The results of these studies are summarized in Table X below. The expression $HL(ED_{50})$ mg./kg. s.c. is an expression of the number of milligrams per kilogram of body weight of the drug administered subcutaneously required to reduce the antibody activity by 50% when compared with a control. In this case, the lower the $HL(ED_{50})$ value for a drug the more effective immunosuppressant it is.

The D.H.S. $(ED_{60})$ mg./kg. s.c. value appearing in column 3 in an expression of the effectiveness of the drug in reducing the edema that accompanies the cell-mediated immune response. It is a measure of the number of milligrams per kilogram of body weight of the drug administered subcutaneously which is required to reduce the edema of the cell-mediated immune response by 60% when compared to the control. Again, the lower the D.H.S. $(ED_{60})$ value the more effective is the drug as an immunosuppressant for the cell-mediate immune response.

TABLE X

| Compound No. | $HL(ED_{50})$ mg/kg, s.c. | D.H.S. $(ED_{60})$ mg/kg, s.c. |
|---|---|---|
| 151 | 0.3 | 1.52 |
| 140 | 0.26 | 1.15 |
| 131 | 18 | 81 |
| 116 | >50 | 56 |
| 117 | >50 | 46 |
| 118 | >50 | 43 |
| 109 | >50 | >50 |
| 110 | — | 50 |
| 3 | 50 | 50 |
| 66 | 46 | >50 |
| 147 | 0.027 | 1.7 |
| 134 | 0.5 | 7.2 |

TABLE X-continued

| Compound No. | HL(ED$_{50}$) mg/kg, s.c. | D.H.S. (ED$_{60}$) mg/kg, s.c. |
|---|---|---|
| 137 | <0.125 | 3.2 |
| 135 | 0.033 | 0.22 |
| 142 | 0.20 | 4.2 |
| 136 | 2.7 | >50 |
| 133 | 0.75 | 32 |
| 139 | 3.0 | >50 |
| 138 | 0.72 | 27 |
| 127 | >50 | 36 |
| 170 | 6.6 | >50 |
| 150 | 22 | >50 |
| 143 | 0.36 | 1.3 |
| 174 | 0.61 | 8.0 |
| 171 | 0.96 | 59.0 |
| 175 | 0.09 | 5.9 |
| 178 | 11.0 | 46.0 |
| 196 | 0.42 | 45.0 |
| 197 | 1.6 | 37 |
| 3 | 50.0 | 50.0 |
| 169 | 46 | >50.0 |
| 146 | 0.11 | 3.1 |
| 153 | 1.2 | 5.7 |
| 149 | 0.16 | 8.8 |
| 126 | 35.0 | >50.0 |
| 177 | 13.0 | >50.0 |
| 182 | 1.1 | — |
| 162 | 13.0 | — |
| 173 | — | 40 |
| 159 | 3.0 | 27 |
| 181 | 16.0 | — |
| 180 | 5.6 | — |
| 183 | 0.39 | 15 |
| 158 | 1.0 | 7.6 |
| 157 | 0.39 | 12 |
| 218 | 1.5 | 25 |
| 219 | 2.5 | >32 |
| 220 | 2.3 | 11 |
| 222 | 1.0 | >32 |

>50 means that it would take more than 50 mg./kg. of drug to reduce the humeral antibody activity by 50% or to reduce edema of the cell mediated immune response by 60%. Since these values are higher than is of practical interest from a clinical point of view, no further testing was doe for these materials.

A number of compounds encompassed in the present invention display non-steroidal anti-inflammatory properties. This appears to be generally the case for the 4-substituted imidazo[1,2-a]quinoxalines of formula 1 above and the 1-(2-acylaminophenyl)imidazoles of formula II. Because of this characteristic, they are indicated for use in the treatment of diseases that the prior art recognizes may be helped by the administration of non-steroidal anti-inflammatory compounds. These include such conditions as ichthyosis, psoriasis, alopecia, atopic eczemas, etc.

The dosage level for administering the anti-inflammatory agents of the present invention may vary somewhat depending on the particular drug selected, the disease being treated and the mode of administration. In general, however, when used for topical application, the compounds are distributed in a pharmaceutical vehicle suitable for topical application. In these compositions, the anti-inflammatory agent of this invention will comprise about 0.5% to 15.0% by weight based on the total weight of the composition.

The anti-inflammatory agents of the present invention may also be administered orally, intraveneously, subcutaneously, intramuscularly, and intradermally. In these cases, the daily dosage will be in the range of from 0.5 mg. to 20 mg. per kilogram of body weight of the active anti-inflammatory agents of this invention.

The anti-inflammatory activity of representative compounds of this invention was determined by the rat paw edema assay both by local administration (Table XI below) and by oral dosing (Table XII below). For the oral dosing, the procedure of C. A. Winter, E. A. Risley and G. W. Nuss, Proc. Soc. Exp. Biol. Med. 111, 544 (1962) was employed with measurement taken four hours after the drug was administered. The local administration tests were carried out similarly except the irritant (carrageenan) and the test compound were injected simultaneously at time zero.

Tables XI and XII report the anti-inflammatory activity of the compounds tested as % difference in the edema or swelling as compared with the control. These Tables also give the response in many instances of more than one dose level of the same drug.

TABLE XI

Rat Paw Edema Assay, Local Administration (injected directly into paw) % Difference from Control

| Compound No. | 1 µg | 10 µg | 100 µg | 100 mg/kg |
|---|---|---|---|---|
| 148 | −32.6 | −53.5 | −14.3 | −39 |
| 109 | −30.3 | −3.9 | +31.6 | |
| 114 | −68.2 | −30.0 | −131.6 | |
| 117 | | | | |
| 110 | | | | −74 |
| 122 | | | | −61 |
| 49 | | | | −35 |
| 7 | | | | −22 |
| 51 | | | | −57 |
| 140 | | | | −78 |

TABLE XII

Rat Paw Edema Assay, Oral Dosing % Difference from Control

| Compound No. | 100 mg/kg | 400 mg/kg |
|---|---|---|
| Indomethacin | −65 | |
| phenybutazone | −76 | |
| Aspirin | −57 | |
| 114 | −61 | |
| 110 | −43 | |
| 122 | −61 | |
| 148 | −52 | |
| 49 | −35 | |
| 7 | −52 | |
| 51 | −57 | |
| 140 | −35 | |
| 131 | −52 | |
| 10 | −30 | |
| 39 | −50 | |
| 133 | −17 | |
| 137 | −26 | |
| 112 | −17 | −68 |
| 111 | −43 | |
| 121 | −61 | |
| 147 | −39 | |
| 134 | −43 | |
| 139 | −22 | −25 |
| 132 | −76 | |
| 150 | −30 | |
| 144 | −26 | |
| 115 | +70 | −25 |
| 117 | −7 | −18 |
| 123 | 0 | −50 |
| 116 | +104 | −18 |
| 136 | −9 | −25 |
| 8 | −22 | −13 |
| 29 | −24 | −25 |
| 14 | −52 | |
| 20 | −59 | |
| 38 | −41 | |
| 57 | −35 | |
| 50 | −20 | −33 |
| 45 | −33 | |
| 40 | −43 | |
| 35 | −50 | |
| 37 | −35 | |
| 18 | −28 | |
| 15 | −24 | −5 |

TABLE XII-continued

Rat Paw Edema Assay, Oral Dosing

| Compound No. | % Difference from Control | |
|---|---|---|
| | 100 mg/kg | 400 mg/kg |
| 55 | −26 | |
| 52 | −26 | |
| 2 | −26 | +43 |
| 23 | −46 | |
| 25 | −30 | |
| 30 | +9 | −33 |
| 36 | −7 | −68 |
| 42 | −9 | −25 |
| 24 | −17 | −25 |
| 109 | −17 | |
| 71 | −22 | |
| 75 | −30 | |
| 68 | −26 | |
| 73 | −22 | |
| 128 | −39 | |
| 129 | −30 | |

What is claimed is:

1. A 1-(2-acylaminophenyl)imidazole of the formula

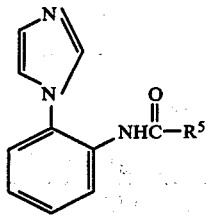

wherein:
R$^5$ is selected from the group consisting of straight chain alkyl of from 1 to 17 carbon atoms, branched chain alkyl of from 4 to 7 carbon atoms, 9-deceneyl, 8,11-eccosadieneyl, C$_1$ to C$_3$ alkyl substituted with halogen or alkoxy, phenoxymethyl and styryl.

2. A 1-(2-acylaminophenyl)imidazole of the formula:

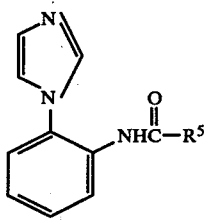

wherein:
R$^5$ is selected from the group consisting of methyl, ethyl, n-propyl, n-butyl, n-pentyl, n-hexyl, n-heptyl, n-octyl, n-nonyl, pentadecyl, heptadecyl, 9-deceneyl, 8,11-eicosadieneyl, t-butyl, isobutyl, 2-ethyl pentyl, chloromethyl, 1-chloroethyl, dichloromethyl, trifluoromethyl, methoxymethyl, styryl and phenoxymethyl.

3. A compound according to claim 2 in which the compound is 1-(2-acetamidophenyl)imidazole.

4. A compound according to claim 2 in which the compound is 1-(2-propionamidophenyl)imidazole.

5. A compound according to claim 2 in which the compound is 1-(2-butyramidophenyl)imidazole.

6. A compound according to claim 2 in which the compound is 1-(2-valeramidophenyl)imidazole.

7. A compound according to claim 2 in which the compound is 1-(2-hexanamidophenyl)imidazole.

8. A compound according to claim 2 in which the compound is 1-(2-heptanamidophenyl)imidazole.

9. A compound according to claim 2 in which the compound is 1-(2-octanamidophenyl)imidazole.

10. A compound according to claim 2 in which the compound is 1-(2-nonanamidophenyl)imidazole.

11. A compound according to claim 2 in which the compound is 1-(2-decanamidophenyl)imidazole.

12. A compound according to claim 2 in which the compound is 1-(2-hexadecanamidophenyl)imidazole.

13. A compound according to claim 2 in which the compound is 1-(2-stearamidophenyl)imidazole.

14. A compound according to claim 2 in which the compound is 1-(2-undec-10-eneamidophenyl)imidazole.

15. A compound according to claim 2 in which the compound is 1-(2-linoleoylamidophenyl)imidazole.

16. A compound according to claim 2 in which the compound is 1-(2-trimethylacetamidophenyl)imidazole.

17. A compound according to claim 2 in which the compound is 1-(2-isovaleramidophenyl)imidazole.

18. A compound according to claim 2 in which the compound is 1-[2-(2-ethylhexanamido)phenyl]-imidazole.

19. A compound according to claim 2 in which the compound is 1-(2-chloroacetamidophenyl)imidazole.

20. A compound according to claim 2 in which the compound is 1-[2-(chloropropionamido)phenyl]imidazole.

21. A compound according to claim 2 in which the compound is 1-(2-dichloroacetamidophenyl)imidazole.

22. A compound according to claim 2 in which the compound is 1-[2-trifluoroacetamido]phenylimidazole.

23. A compound according to claim 2 in which the compound is 1-(2-methoxyacetamidophenyl)imidazole.

24. A compound according to claim 2 in which the compound is 1-(2-phenoxyacetamidophenyl)imidazole.

* * * * *